United States Patent [19]

Jakobson et al.

[11] Patent Number: 4,973,763

[45] Date of Patent: Nov. 27, 1990

[54] PROCESS FOR THE PREPARATION OF POLYGLYCEROLS

[75] Inventors: Gerald Jakobson; Horst Linke; Werner Siemanowsky, all of Rheinberg, Fed. Rep. of Germany

[73] Assignee: Deutsche Solvay-Werke GmbH, Solingen, Fed. Rep. of Germany

[21] Appl. No.: 403,831

[22] Filed: Sep. 5, 1989

Related U.S. Application Data

[63] Continuation of Ser. No. 211,435, Jun. 24, 1988, abandoned.

[30] Foreign Application Priority Data

Jun. 25, 1987 [DE] Fed. Rep. of Germany ....... 3721003
Apr. 8, 1988 [DE] Fed. Rep. of Germany ....... 3811826

[51] Int. Cl.$^5$ .................... C07C 41/01; C07C 37/70
[52] U.S. Cl. .................................. 568/619; 568/679; 568/680; 568/699
[58] Field of Search ............... 568/679, 680, 699, 619

[56] References Cited

U.S. PATENT DOCUMENTS 2,520,670  8/1950  Wittcoff et al. ................ 568/679

FOREIGN PATENT DOCUMENTS 3410520  9/1985  Fed. Rep. of Germany .

OTHER PUBLICATIONS

Kirk-Othmer, Encyclopedia of Chemical Technology, 2nd edition, vol. 5, pp. 311-318, 1964.

*Primary Examiner*—Howard T. Mars
*Attorney, Agent, or Firm*—Foley & Lardner, Schwartz, Jeffery, Schwaab, Mack, Blumenthal & Evans

[57] ABSTRACT

A process for preparation of polyglycerol is provided, comprising the steps of (a) reacting glycerol or diglycerol with hydrogen chloride at between about 340° K. and about 410° K. to yield a mixture that comprises an α-monochlorohydrin of glycerol or an α-monochlorohydrin of diglycerol, (b) mixing the α-monochlorohydrins and an alkali metal glycerolate or an alkali metal diglycerolate at a temperature of between about 320° K. and 410° K. to yield a mixture of alkali metal chloride and glycerol and/or diglycerol and polyglyerol, (c) separating the alkali metal chloride from the glycerols and (d) separating the polyglycerol from glycerol and/or diglycerol.

24 Claims, No Drawings

1

PROCESS FOR THE PREPARATION OF POLYGLYCEROLS

This application is a continuation of application Ser. No. 07/211,435, filed June 24, 1988, now abandoned.

BACKGROUND OF THE INVENTION

The present invention relates to a process for the preparation of polygylcerols by reaction of glycerols in the presence of heat. In the context of the present invention "polyglycerol" denotes a compound that comprises more than two glycerol units; and glycerol, diglycerol or other polyglycerols are collectively referred to as "glycerols."

A process for the preparation of polyglycerols (optionally having a low content of cyclic components) by acid-catalyzed reaction of glycerols in the presence of heat has already been disclosed in DE-OS (German Offenlegungsschrift) No. 2,455,327, in which the glycerol is condensed to polyglycerols at below 20 mm Hg in the presence of sulfuric acid and glycerol acetate. The formation of by-products such as acrolein and sulfuric acid esters is disadvantageous in this process. A further disadvantage consists of the necessary use of absolutely pure glycerol, since otherwise a strong discoloration of the batch by the hot sulfuric acid takes place.

SUMMARY OF THE INVENTION

It is therefore an object of the present invention to avoid these disadvantages and to find a process that facilitates the preparation of polyglycerols with few requirements in terms of apparatus and also without further addition of auxiliary chemicals.

It is another object of the present invention to produce polyglycerol that has a low content of cyclic components.

It is still another object of the present invention to produce polyglycerol without the use of sulfuric acid.

In accomplishing these and other objects, there has been provided a process for preparation of polyglycerol comprising the steps of (a) reacting at least one of glycerol and diglycerol with either gaseous hydrogen chloride or concentrated hydrochloric acid at a temperature of between about 340° K. and 410° K. to produce a first mixture containing (i) α-monochlorohydrin of glycerol and/or diglycerol and (ii) glycerol and/or diglycerol;

(b) adding the first mixture or the α-monochlorohydrin of glycerol and/or diglycerol separated from the first mixture of an alkali metal glycerolate and/or an alkali metal diglycerolate, at a temperature of between about 320° K. and about 410° K., to produce a second mixture containing glycerol and/or diglycerol, polyglycerol and alkali metal chloride;

(c) separating the alkali metal chloride from the second mixture; and (d) separating the glycerol and/or diglycerol from the polyglycerol.

Further objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

According to one aspect of the present invention, it has been ascertained that these aims are fulfilled by a process for the preparation of polyglycerols (optionally having a low content of cyclic components) by reaction of glycerols in the presence of heat, in which at least one of glycerol and diglycerol is reacted, at a temperature of between about 340° K. and about 410° K., with gaseous hydrogen chloride or concentrated hydrochloric acid to give a mixture composed essentially of α-monochlorohydrin of glycerol and/or diglycerol, and glycerol and/or diglycerol, and the resultant mixture or the α-monochlorohydrin of glycerol and/or diglycerol separated off from the mixture is added at a temperature of between about 320° K. and about 410° K. to at least one of an alkali metal glycerolate and an alkali metal diglycerolate, after which the glycerol and/or diglycerol/polyglycerol mixture thus prepared is separated from the resultant alkali metal chlorides and the glycerol and/or diglycerol is separated from the polyglycerol.

The reaction of glycerol and/or diglycerol with gaseous hydrogen chloride or concentrated hydrochloric acid takes place in this connection in the presence of a catalyst, preferably a liquid saturated $C_1$–$C_3$ carboxylic acid, at a concentration of the catalyst (relative to the total amount by weight of glycerol and/or diglycerol employed) of about 0.05% to about 3% by weight, preferably about 0.5% to about 2% by weight.

According to another preferred embodiment of the process according to the invention, the glycerol and/or diglycerol is reacted in the presence of a catalyst at temperatures of between about 340° K. and about 410° K. with gaseous hydrogen chloride or concentrated hydrochloric acid and the resultant mixture or the α-monochlorohydrin of glycerol and/or diglycerol separated off from the mixture is added at temperatures of between about 320° K. and about 410° K. to an alkali metal glycerolate and/or an alkali metal diglycerolate that contains an alkaline-reacting substance (base), preferably alkali metal hydroxide, after which the glycerol and/or diglycerol/polyglycerol mixture thus prepared is separated from the resultant alkali metal chlorides and the glycerol and/or diglycerol is separated from the polyglycerol.

According to another preferred embodiment of the present invention, the glycerol and/or diglycerol to be reacted with gaseous hydrogen chloride or concentrated hydrochloric acid has a glycerol and/or diglycerol content of more than about 80% by weight, preferably more than about 90% by weight. The unreacted glycerol and, optionally, a portion of the diglycerol is preferably separated from the polyglycerol by fractional distillation.

The alkali metal glycerolate and/or alkali metal diglycerolate suitable for use in the present invention has an alkali metal glycerolate or alkali metal diglycerolate content of more than about 80% by weight, preferably more than about 90% by weight, and preferably additionally contains an alkaline-reacting constituent, preferably an alkali metal hydroxide.

In the context of the present invention, pure hydrogen chloride or a hydrogen chloride gas mixture, preferably a hydrogen chloride gas mixture that is produced in the preparation of vinyl chloride and/or allyl chloride, is employed as the hydrogen chloride gas.

A hydrochloric acid that has a content of about 10% to about 40% by weight, preferably 30% to 35% by weight, of HCL is employed as the concentrated hydrochloric acid. According to a preferred embodiment of the process according to the invention, the α-monochlorohydrin of glycerol and/or diglycerol is added to the initially-introduced glycerolate and/or diglycerolate with stirring, preferably by continuous addition.

According to a preferred embodiment of the process according to the invention, the α-monochlorohydrin of glycerol and/or diglycerol is simultaneously introduced into a preferably thermostabilized straight-through reactor continuously with the glycerolate and/or diglycerolate, by means of which short reaction times can be achieved.

After the reaction is complete or after the formation of the polyglycerols, a portion of the resultant alkali metal chloride is preferably separated off as a solid by physical processes that are known per se, preferably by sedimentation and/or centrifugation. The remaining portion is preferably separated off from the resultant polyglycerol mixture through an ion exchanger after the addition of water in a manner known per se, for example according to the process of DE-OS (German Offenlegungsschrift) No. 3,410,520.

Furthermore, it is intended that an improved purification of the glycerol and/or diglycerol/polyglycerol mixture obtained according to the invention can be achieved.

According to the invention, the purification of the glycerol and/or diglycerol/polyglycerol mixture obtained takes place by dilution with water to a solution of about 70% to about 40% strength by weight, preferably about 60% to about 50% strength by weight, which is desalted at temperatures of about 30° C. to about 80° C., preferably about 40° C. to about 60° C., through a combination of strongly acidic cation exchangers and subsequent weakly basic anion exchangers.

The regeneration of the cation exchanger material in the cation exchangers preferably takes place by means of a parallel current or combined parallel current regeneration.

According to a preferred embodiment, the salts are washed out after the regeneration. After completion of the washing-out process, the polyglycerol-containing, preferably diglycerol-containing, solution is passed through the ion exchanger and the polyglycerol-containing, preferably diglycerol-containing, solution leaving the anion exchanger is passed through again until a polyglycerol content, preferably a diglycerol content, of about 20% by weight, is achieved, preferably until a polyglycerol content, preferably a diglycerol content, of about 15% by weight, is achieved and is also used for the preparation of the approximately 70%–40% strength by weight, preferably approximately 60%–50% strength by weight, polyglycerol-containing, preferably diglycerol-containing starting solution.

The passage of the polyglycerol-containing, preferably diglycerol-containing, solution through the ion exchanger preferably takes place under an increased pressure. In this connection, the polyglycerol-containing, preferably diglycerol-containing, solution is passed through the ion exchanger, i.e. through one or more cation exchangers and at least one anion exchanger under a pressure of about 1.1–about 10 bar, preferably about 2–6 bar. Valves are mounted on one or more sites in the tubing or on the ion exchangers for controlling and maintaining the pressure.

In this connection, the polyglycerol-containing, preferably diglycerol-containing, solution is expediently passed through the ion exchanger at a flow rate of about 0.5 m/h to about 15 m/h, preferably about 1 m/h to about 5 m/h.

Cation exchanger materials and anion exchanger materials preferably used are those which are temperature-resistant to above about 80° C., preferably to above about 100° C.

The ion exchanger material of the cation exchanger and/or anion exchanger is expediently covered by a sieve plate, perforated plate or a device arranged so it can be slid along the vertical axis of the ion exchanger, covering the exchanger material and facilitating uniform passage of liquid, and/or an inert molded material and/or elastic synthetic material.

The strongly acidic cation exchanger material and the weakly basic anion exchanger material preferably possess an internal surface area (measured by the BET method) of more than about 25 $m^2/g$, preferably about 50 to about 100 $m^2/g$.

The present invention is further described below by reference to the following examples.

EXAMPLE 1

Hydrogen chloride was introduced for 2.5 hours at about 383° K. into a solution of 1.104 kg of 99.5% strength glycerol (12 mol) and 31.5 g of 35% strength acetic acid, as a result of which the increase in weight was about 40%. 500 g of this solution was introduced with stirring during the course of 1.25 hours into a reactor, in which 92 g (1 mol) of glycerol, 269.4 g of 50% strength sodium hydroxide solution and 160 ml of distilled water were present at 393° K.

After a further 5 hours, the reaction mixture was diluted with distilled water, desalted through an ion exchanger and subsequently evaporated in vacuo.

The product mixture has the following composition (in per cent by weight):

Glycerol 29.1, cyclic diglycerol 1.2, diglycerol 31.7, cyclic triglycerol 1.7, triglycerol 17.1, cyclic tetraglycerol 0.9, tetraglycerol 9.1, cyclic pentaglycerol 0.1, pentaglycerol 4.9, hexaglycerol 2.8 and heptaglycerol 1.3.

EXAMPLE 2

111 g (1 mol) of α-monochlorohydrin was introduced with stirring into a reactor, in which 92 g (1 mol) of glycerol and 81 g of a 50% strength sodium hydroxide solution (1.1 mol) were present at about 343° to about 358° K. After 5 minutes, the reaction mixture was diluted with distilled water, desalted through an ion exchanger and subsequently evaporated in vacuo. The product mixture had the following composition (in % by weight): glycerol 35.0, cyclic diglycerol 0.3, diglycerol 33.5, cyclic triglycerol 0.2, triglycerol 18.0, cyclic tetraglycerol 0.1, tetraglycerol 8.4, pentaglycerol 3.4, hexaglycerol 1.2 and heptaglycerol 0.1.

EXAMPLE 3

111 g (1 mol) of α-monochlorohydrin was introduced with stirring into a reactor, in which 166 g (1 mol) of diglycerol and 88 g of a 55% strength sodium hydroxide solution (1.1 mol) were present between about 343°–358° K. After 5 minutes, the reaction mixture was diluted with distilled water, desalted through an ion exchanger and subsequently evaporated in vacuo.

The product mixture had the following composition (in % by weight): glycerol 4.5, cyclic diglycerol 0.1, diglycerol 35.4, cyclic triglycerol 0.2, triglycerol 30.8, cyclic tetraglycerol 0.1, tetraglycerol 17.5, pentaglycerol 8.0, hexaglycerol 3.0 and heptaglycerol 0.4.

EXAMPLE 4

The polyglycerol and/or diglycerol prepared by the process according to the invention is diluted with water to a solution of about 55% strength by weight polyglycerol, preferably diglycerol solution.

The solution obtained is passed at a temperature between about 40° C. to about 60° C. successively through a strongly acidic ion exchanger containing an ion exchanger material that is arranged over a sieve bottom or nozzle bottom.

The polyglycerol-containing, preferably diglycerol-containing, solution leaving the sieve bottom enters into the ion exchanger container connected downstream, in which a weakly basic ion exchanger material is arranged above the nozzle bottom or sieve bottom, which is overlaid by an inert molded material. The aqueous solution emerging from the anion exchanger having a salt content of less than about 0.5% by weight is transferred to a distillation plant and separated by fractional distillation.

What is claimed is:

1. A process for preparation of polyglycerol, comprising the steps of
   (a) reacting at least one of glycerol and diglycerol with either gaseous hydrogen chloride or concentrated hydrochloric acid, at a temperature of between about 340° K. and 410° K., to produce a first mixture containing (i) α-monochlorohydrin of glycerol and/or diglycerol and (ii) glycerol and/or diglycerol;
   (b) adding said first mixture or the α-monochlorohydrin of glycerol and/or diglycerol separated from said first mixture to an alkali metal glycerolate and/or an alkali metal diglycerolate having a content of said alkali metal glycerolate and/or alkali metal diglycerolate of more than 80% by weight, at a temperature of between about 320° K. and 410° K., and additionally in the presence of a base, to produce a second mixture containing glycerol and/or diglycerol, polyglycerol and alkali metal chloride;
   (c) physically separating as a solid by sedimentation or centrifugation a portion of the alkali metal chloride in said second mixture;
   (d) diluting said second mixture with water to form an aqueous solution having a total concentration of glycerol, diglycerol and polyglycerol of about 70% to 40% by weight;
   (e) desalting said solution, at a temperature of between about 30° C. and 80° C., and by first passing the solution through a strongly acidic cation exchanger and then through a weakly basic anion exchanger; and
   (f) separating the glycerol and/or diglycerol from the polyglycerol in the effluent from the anion exchanger.

2. A process as claimed in claim 1, consisting essentially of the recited steps.

3. A process as claimed in claim 1, wherein step (a) is carried out in the presence of a catalyst, said catalyst being a liquid, saturated $C_1$-$C_3$ carboxylic acid; and wherein said catalyst is present at a concentration, relative to the total amount by weight of glycerol and/or diglycerol, of about 0.05% to about 3% by weight.

4. A process as claimed in claim 1, wherein in step (b), said base is an alkali metal hydroxide.

5. A process as claimed in claim 1, wherein in step (a) the concentration of the glycerol and/or diglycerol that is reacted with hydrogen chloride or hydrochloric acid is more than 80% by weight.

6. A process as claimed in claim 1, wherein in step (b), said alkali metal glycerolate and/or alkali metal diglycerolate has a concentration of more than 90% by weight.

7. A process as claimed in claim 1, wherein in step (a) the gaseous hydrogen chloride is either pure hydrogen chloride or a mixture comprising hydrogen chloride gas.

8. A process as claimed in claim 7, wherein the mixture comprising hydrogen chloride gas is produced in the preparation of vinyl chloride and/or allyl chloride.

9. A process as claimed in claim 1, wherein in step (a), the concentration hydrochloric acid has a concentration of about 10% to about 40% by weight.

10. A process as claimed in claim 1, wherein in step (b), the α-monochlorhydrin of glycerol and/or diglycerol and the glycerolate and/or diglycerolate are introduced into a flow reactor simultaneously.

11. A process as claimed in claim 1, wherein in step (e), said cation exchanger comprises a cation exchanger material, and the process further comprises the step of regenerating the cation exchange material by means of a parallel current or combined parallel current regeneration after passage therethrough of said aqueous solution.

12. A process as claimed in claim 11, wherein said regeneration further comprises the step of washing the salts out of the cation exchanger after regeneration.

13. A process as claimed in claim 1, wherein in step (e), said desalting is carried out at an elevated pressure of about 1.1 to about 10 bar.

14. A process as claimed in claim 1, wherein in step (e), each ion exchanger comprises an ion exchange material, and wherein each said ion exchange material is covered by at least one of (a) a sieve plate or a perforated plate, (b) an inert molded material, and (c) an elastic synthetic material.

15. A process as claimed in claim 1, wherein in step (e), the cation exchange material and anion exchange material used in said ion exchangers are each temperature-resistant to above 80° C.

16. A process as claimed in claim 1, wherein in step (e), each of the ion exchange resins used in said ion exchangers has an internal surface area of more than 25 $m^2/g$.

17. A process as claimed in claim 1, wherein in step (e), said aqueous solution is passed through the ion exchangers at a flow rate of about 0.5 m/h to about 15 m/h.

18. A process as claimed in claim 1, wherein in step (e), said aqueous solution has a total concentration of glycerol, diglycerol and polyglycerol of about 60% to 50% by weight.

19. A process as claimed in claim 1, wherein in step (e), said desalting is effected at a temperature of from 40° C. to 60° C.

20. A process as claimed in claim 3, wherein in step (a), the concentration of said catalyst is about 0.5% to about 2% by weight.

21. A process as claimed in claim 5, wherein the concentration of the glycerol and/or diglycerol that is reacted with hydrogen chloride or hydrochloric acid is more than 90% by weight.

22. A process as claimed in claim 9, wherein the concentrated hydrochloric acid has a concentration of about 30% to about 35% by weight.

23. A process as claimed in claim 12, wherein after said washing step, a portion of said second mixture containing glycerol and/or diglycerol, polyglycerol and alkali metal chloride resulting from step (b) is cycled through said ion exchangers until its total glycerols concentration is reduced to about 20% by weight, after which the recycle effluent is used in step (d) to dilute more of said second mixture and form said aqueous solution.

24. A process as claimed in claim 23, wherein the total glycerols content of said recycle effluent is reduced to about 15% by weight.

* * * * *